(12) United States Patent
Wellig

(10) Patent No.: US 12,142,382 B2
(45) Date of Patent: Nov. 12, 2024

(54) AIRBORNE INFECTION EARLY WARNING SYSTEM

(71) Applicant: Honeywell International Inc., Charlotte, NC (US)

(72) Inventor: Armin Wellig, Mont-sur-Rolle (CH)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 740 days.

(21) Appl. No.: 17/188,790

(22) Filed: Mar. 1, 2021

(65) Prior Publication Data

US 2022/0277851 A1   Sep. 1, 2022

(51) Int. Cl.
*G16H 50/30* (2018.01)
*F24F 11/30* (2018.01)
(Continued)

(52) U.S. Cl.
CPC ............ *G16H 50/30* (2018.01); *F24F 11/30* (2018.01); *F24F 11/523* (2018.01); *F24F 11/56* (2018.01);
(Continued)

(58) Field of Classification Search
CPC ......... G16H 50/30; G16H 50/80; F24F 11/30; F24F 11/523; F24F 11/56; F24F 2110/10;
(Continued)

(56) References Cited

U.S. PATENT DOCUMENTS

| 191,512 A | 6/1877 | Bennett et al. |
| 4,009,647 A | 3/1977 | Howorth |

(Continued)

FOREIGN PATENT DOCUMENTS

| CA | 2387100 A1 | 11/2003 |
| CA | 2538139 A1 | 3/2005 |

(Continued)

OTHER PUBLICATIONS

Bocicor et al. "Wireless Sensor Network based System for the Prevention of Hospital Acquired Infections", arxiv.org, Cornell University Ithaca, NY 14853, May 2, 2017, XP080947042, (Abstract).

(Continued)

*Primary Examiner* — Charles R Kasenge
(74) *Attorney, Agent, or Firm* — Seager, Tufte & Wickhem, LLP

(57) ABSTRACT

A method for reducing risks of airborne infection within a facility having a Building Management System (BMS) with a plurality of sensors disposed within the facility configured to measure a plurality of different healthy building parameters that impact risk of airborne infection includes a controller receiving values for a plurality of different healthy building parameters and applying the values of the plurality of different healthy building parameters to a risk model that processes the values of the plurality of different healthy building parameters in order to ascertain an airborne infection risk score for at least part of the facility and one or more suggested changes to a current operation of the BMS system in order to reduce the airborne infection risk score.

18 Claims, 9 Drawing Sheets

(51) Int. Cl.
*F24F 11/523* (2018.01)
*F24F 11/56* (2018.01)
*G16H 50/80* (2018.01)
*F24F 110/10* (2018.01)
*F24F 110/20* (2018.01)
*F24F 110/65* (2018.01)

(52) U.S. Cl.
CPC .......... *G16H 50/80* (2018.01); *F24F 2110/10* (2018.01); *F24F 2110/20* (2018.01); *F24F 2110/65* (2018.01)

(58) Field of Classification Search
CPC ............... F24F 2110/20; F24F 2110/65; F24F 2110/64; F24F 11/62; F24F 2110/50; F24F 2110/66; F24F 2110/70; F24F 2110/72; F24F 2110/74
See application file for complete search history.

(56) References Cited

U.S. PATENT DOCUMENTS

| | | |
|---|---|---|
| 4,375,637 A | 3/1983 | Desjardins |
| 4,918,615 A | 4/1990 | Suzuki et al. |
| 4,939,922 A | 7/1990 | Smalley et al. |
| 5,566,084 A | 10/1996 | Cmar |
| 5,727,579 A | 3/1998 | Chardack |
| 5,745,126 A | 4/1998 | Jain et al. |
| 5,751,916 A | 5/1998 | Kon et al. |
| 5,777,598 A | 7/1998 | Gowda et al. |
| 5,973,662 A | 10/1999 | Singers et al. |
| 6,065,842 A | 5/2000 | Fink |
| 6,139,177 A | 10/2000 | Venkatraman et al. |
| 6,144,993 A | 11/2000 | Fukunaga et al. |
| 6,157,943 A | 12/2000 | Meyer |
| 6,229,429 B1 | 5/2001 | Horon |
| 6,238,337 B1 | 5/2001 | Kambhatla et al. |
| 6,334,211 B1 | 12/2001 | Kojima et al. |
| 6,353,853 B1 | 3/2002 | Gravlin |
| 6,369,695 B2 | 4/2002 | Horon |
| 6,375,038 B1 | 4/2002 | Daansen et al. |
| 6,429,868 B1 | 8/2002 | Dehner, Jr. et al. |
| 6,473,084 B1 | 10/2002 | Phillips et al. |
| 6,487,457 B1 | 11/2002 | Hull et al. |
| 6,580,950 B1 | 6/2003 | Johnson et al. |
| 6,598,056 B1 | 7/2003 | Hull et al. |
| 6,619,555 B2 | 9/2003 | Rosen |
| 6,704,012 B1 | 3/2004 | Lefave |
| 6,712,269 B1 | 3/2004 | Watkins |
| 6,720,874 B2 | 4/2004 | Fufido et al. |
| 6,741,915 B2 | 5/2004 | Poth |
| 6,796,896 B2 | 9/2004 | Laiti |
| 6,801,199 B1 | 10/2004 | Wallman |
| 6,816,878 B1 | 11/2004 | Zimmers et al. |
| 6,876,951 B2 | 4/2005 | Skidmore et al. |
| 6,882,278 B2 | 4/2005 | Winings et al. |
| 6,904,385 B1 | 6/2005 | Budike, Jr. |
| 6,907,387 B1 | 6/2005 | Reardon |
| 6,911,177 B2 | 6/2005 | Deal |
| 6,993,403 B1 | 1/2006 | Dadebo et al. |
| 6,993,417 B2 | 1/2006 | Osann, Jr. |
| 7,023,440 B1 | 4/2006 | Havekost et al. |
| 7,031,880 B1 | 4/2006 | Seem et al. |
| 7,062,722 B1 | 6/2006 | Carlin et al. |
| 7,110,843 B2 | 9/2006 | Pagnano et al. |
| 7,139,685 B2 | 11/2006 | Bascle et al. |
| 7,164,972 B2 | 1/2007 | Imhof et al. |
| 7,183,899 B2 | 2/2007 | Behnke |
| 7,200,639 B1 | 4/2007 | Yoshida |
| 7,222,111 B1 | 5/2007 | Budike, Jr. |
| 7,222,800 B2 | 5/2007 | Wruck |
| 7,257,397 B2 | 8/2007 | Shamoon et al. |
| 7,280,030 B1 | 10/2007 | Monaco |
| 7,292,908 B2 | 11/2007 | Borne et al. |
| 7,295,116 B2 | 11/2007 | Kumar et al. |
| 7,302,313 B2 | 11/2007 | Sharp et al. |
| 7,308,323 B2 | 12/2007 | Kruk et al. |
| 7,308,388 B2 | 12/2007 | Beverina et al. |
| 7,313,447 B2 | 12/2007 | Hsiung et al. |
| 7,346,433 B2 | 3/2008 | Budike, Jr. |
| 7,356,548 B1 | 4/2008 | Culp et al. |
| 7,379,782 B1 | 5/2008 | Cocco |
| 7,383,148 B2 | 6/2008 | Ahmed |
| 7,434,742 B2 | 10/2008 | Mueller et al. |
| 7,447,333 B1 | 11/2008 | Masticola et al. |
| 7,466,224 B2 | 12/2008 | Ward et al. |
| 7,496,472 B2 | 2/2009 | Seem |
| 7,512,450 B2 | 3/2009 | Ahmed |
| 7,516,490 B2 | 4/2009 | Riordan et al. |
| 7,548,833 B2 | 6/2009 | Ahmed |
| 7,551,092 B1 | 6/2009 | Henry |
| 7,557,729 B2 | 7/2009 | Hubbard et al. |
| 7,567,844 B2 | 7/2009 | Thomas et al. |
| 7,596,473 B2 | 9/2009 | Hansen et al. |
| 7,610,910 B2 | 11/2009 | Ahmed |
| 7,626,507 B2 | 12/2009 | LaCasse |
| 7,664,574 B2 | 2/2010 | Imhof et al. |
| 7,682,464 B2 | 3/2010 | Glenn et al. |
| 7,688,212 B2 | 3/2010 | Farley |
| 7,702,421 B2 | 4/2010 | Sullivan et al. |
| 7,729,882 B2 | 6/2010 | Seem |
| 7,755,494 B2 | 7/2010 | Melker et al. |
| 7,761,310 B2 | 7/2010 | Rodgers |
| 7,774,227 B2 | 8/2010 | Srivastava |
| 7,797,188 B2 | 9/2010 | Srivastava |
| 7,819,136 B1 | 10/2010 | Eddy |
| 7,822,806 B2 | 10/2010 | Frank et al. |
| 7,856,370 B2 | 12/2010 | Katta et al. |
| 7,944,358 B2 | 5/2011 | Sorensen et al. |
| 7,978,083 B2 | 7/2011 | Melker et al. |
| 7,984,384 B2 | 7/2011 | Chaudhri et al. |
| 7,986,323 B2 | 7/2011 | Kobayashi et al. |
| 8,024,666 B2 | 9/2011 | Thompson |
| 8,086,047 B2 | 12/2011 | Penke et al. |
| 8,099,178 B2 | 1/2012 | Mairs et al. |
| 8,151,280 B2 | 4/2012 | Sather et al. |
| 8,176,095 B2 | 5/2012 | Murray et al. |
| 8,218,871 B2 | 7/2012 | Angell et al. |
| 8,219,660 B2 | 7/2012 | McCoy et al. |
| 8,271,941 B2 | 9/2012 | Zhang et al. |
| 8,294,585 B2 | 10/2012 | Barnhill |
| 8,302,020 B2 | 10/2012 | Ouch et al. |
| 8,320,634 B2 | 11/2012 | Deutsch |
| 8,334,422 B2 | 12/2012 | Gutsol et al. |
| 8,344,893 B1 | 1/2013 | Drammeh |
| 8,375,118 B2 | 2/2013 | Hao et al. |
| 8,476,590 B2 | 7/2013 | Stratmann et al. |
| 8,516,016 B2 | 8/2013 | Park et al. |
| 8,558,660 B2 | 10/2013 | Nix et al. |
| 8,639,527 B2 | 1/2014 | Rensvold et al. |
| 8,698,637 B2 | 4/2014 | Raichman |
| 8,816,860 B2 | 8/2014 | Ophardt et al. |
| 8,869,027 B2 | 10/2014 | Louch et al. |
| 8,904,497 B2 | 12/2014 | Hsieh |
| 8,936,944 B2 | 1/2015 | Peltz et al. |
| 8,947,437 B2 | 2/2015 | Garr et al. |
| 8,950,019 B2 | 2/2015 | Loberger et al. |
| 9,000,926 B2 | 4/2015 | Hollock et al. |
| 9,030,325 B2 | 5/2015 | Taneff |
| 9,098,738 B2 | 8/2015 | Bilet et al. |
| 9,105,071 B2 | 8/2015 | Fletcher et al. |
| 9,175,356 B2 | 11/2015 | Peltz et al. |
| 9,240,111 B2 | 1/2016 | Scott et al. |
| 9,280,884 B1 | 3/2016 | Schultz et al. |
| 9,292,972 B2 | 3/2016 | Hailemariam et al. |
| 9,320,662 B2 | 4/2016 | Hayes et al. |
| 9,370,600 B2 | 6/2016 | DuPuis et al. |
| 9,373,242 B1 | 6/2016 | Conrad et al. |
| 9,396,638 B2 | 7/2016 | Wildman et al. |
| 9,311,807 B2 | 8/2016 | Schultz et al. |
| 9,406,212 B2 | 8/2016 | De Luca et al. |
| 9,418,535 B1 | 8/2016 | Felch et al. |
| 9,418,536 B1 | 8/2016 | Felch et al. |
| 9,449,219 B2 | 9/2016 | Bilet et al. |

(56) References Cited

U.S. PATENT DOCUMENTS

| | | |
|---|---|---|
| 9,477,543 B2 | 10/2016 | Henley et al. |
| 9,497,832 B2 | 11/2016 | Verberkt et al. |
| 9,513,364 B2 | 12/2016 | Hall et al. |
| 9,526,380 B2 | 12/2016 | Hamilton et al. |
| 9,526,806 B2 | 12/2016 | Park et al. |
| 9,536,415 B2 | 1/2017 | De Luca et al. |
| 9,558,648 B2 | 1/2017 | Douglas |
| 9,591,267 B2 | 3/2017 | Lipton et al. |
| 9,613,518 B2 | 4/2017 | Dunn et al. |
| 9,618,224 B2 | 4/2017 | Emmons et al. |
| 9,618,918 B2 | 4/2017 | O'Keeffe |
| 9,640,059 B2 | 5/2017 | Hyland |
| 9,672,360 B2 | 6/2017 | Barkan |
| 9,710,700 B2 | 7/2017 | Bilet et al. |
| 9,715,242 B2 | 7/2017 | Pillai et al. |
| 9,721,452 B2 | 8/2017 | Felch et al. |
| 9,729,945 B2 | 8/2017 | Schultz et al. |
| 9,784,464 B2 | 10/2017 | Yamamoto et al. |
| 9,843,743 B2 | 12/2017 | Lewis et al. |
| 9,856,634 B2 | 1/2018 | Rodenbeck et al. |
| 9,872,088 B2 | 1/2018 | Fadell et al. |
| 9,875,639 B2 | 1/2018 | Bone et al. |
| 9,911,312 B2 | 3/2018 | Wildman et al. |
| 9,940,819 B2 | 4/2018 | Ferniany |
| 9,956,306 B2 | 5/2018 | Brais et al. |
| 9,986,175 B2 | 5/2018 | Frank et al. |
| 10,087,608 B2 | 10/2018 | Dobizl et al. |
| 10,223,894 B2 | 3/2019 | Raichman |
| 10,228,837 B2 | 3/2019 | Hua et al. |
| 10,235,865 B2 | 3/2019 | Thyroff |
| 10,251,610 B2 | 4/2019 | Parthasarathy et al. |
| 10,298,411 B2 | 5/2019 | Donlan et al. |
| 10,303,843 B2 | 5/2019 | Bitran et al. |
| 10,332,382 B2 | 6/2019 | Thyroff |
| 10,382,893 B1 | 8/2019 | Wootton et al. |
| 10,469,590 B2 | 11/2019 | Scanlin et al. |
| 10,514,817 B2 | 12/2019 | Hua et al. |
| 10,565,844 B2 | 2/2020 | Pourmohammad et al. |
| 10,602,474 B2 | 3/2020 | Goldstein |
| 10,607,147 B2 | 3/2020 | Raykov et al. |
| 10,613,504 B2 | 4/2020 | Chowdhury |
| 10,691,081 B2 | 6/2020 | Ray et al. |
| 10,708,154 B2 | 7/2020 | Pefkianakis et al. |
| 10,866,003 B2 | 12/2020 | Ajax et al. |
| 10,944,830 B2 | 3/2021 | Scanlin et al. |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0233432 A1 | 12/2003 | Davis et al. |
| 2004/0001009 A1 | 1/2004 | Winings et al. |
| 2004/0064260 A1 | 4/2004 | Padmanabhan et al. |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0067545 A1 | 3/2006 | Lewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0239484 A1 | 10/2007 | Arond et al. |
| 2007/0268122 A1 | 11/2007 | Kow et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0062167 A1 | 3/2008 | Boggs et al. |
| 2008/0067244 A1 | 3/2008 | Marks |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 | 4/2011 | Laycock et al. |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |

(56) References Cited

U.S. PATENT DOCUMENTS

| | | |
|---|---|---|
| 2011/0161124 A1 | 6/2011 | Lappinga et al. |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |
| 2011/0298301 A1 | 12/2011 | Wong et al. |
| 2011/0316703 A1 | 12/2011 | Butler et al. |
| 2011/0320054 A1 | 12/2011 | Brzezowski |
| 2012/0022700 A1 | 1/2012 | Drees et al. |
| 2012/0039503 A1 | 2/2012 | Chen et al. |
| 2012/0062382 A1 | 3/2012 | Taneff |
| 2012/0066168 A1 | 3/2012 | Fadell et al. |
| 2012/0075464 A1 | 3/2012 | Derenne et al. |
| 2012/0109988 A1 | 5/2012 | Li et al. |
| 2012/0112883 A1 | 5/2012 | Wallace et al. |
| 2012/0131217 A1 | 5/2012 | Delorme et al. |
| 2012/0158185 A1 | 6/2012 | El-Mankabady et al. |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0276517 A1 | 11/2012 | Banaszuk et al. |
| 2012/0291068 A1 | 11/2012 | Khushoo et al. |
| 2012/0303652 A1 | 11/2012 | Tseng |
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0086152 A1 | 4/2013 | Hersche et al. |
| 2013/0091631 A1 | 4/2013 | Hayes et al. |
| 2013/0110295 A1 | 5/2013 | Zheng et al. |
| 2013/0169681 A1 | 7/2013 | Rasane et al. |
| 2013/0184880 A1 | 7/2013 | McMahon |
| 2013/0187775 A1 | 7/2013 | Marsden et al. |
| 2013/0204570 A1 | 8/2013 | Mendelson et al. |
| 2013/0229276 A1 | 9/2013 | Hunter |
| 2013/0268293 A1 | 10/2013 | Knudson et al. |
| 2013/0289774 A1 | 10/2013 | Day et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0079282 A1 | 3/2014 | Marcheselli et al. |
| 2014/0167917 A2 | 6/2014 | Wallace et al. |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2015/0025329 A1 | 1/2015 | Amarasingham et al. |
| 2015/0032264 A1 | 1/2015 | Emmons et al. |
| 2015/0056909 A1 | 2/2015 | Chien |
| 2015/0070174 A1 | 3/2015 | Douglas |
| 2015/0077258 A1 | 3/2015 | Nelson et al. |
| 2015/0113462 A1 | 4/2015 | Chen et al. |
| 2015/0153918 A1 | 6/2015 | Chen et al. |
| 2015/0161874 A1 | 6/2015 | Thyroff et al. |
| 2015/0167995 A1 | 6/2015 | Fadell et al. |
| 2015/0168949 A1 | 6/2015 | Hua et al. |
| 2015/0194043 A1 | 7/2015 | Dunn et al. |
| 2015/0198707 A1 | 7/2015 | Al-Alusi |
| 2015/0212717 A1 | 7/2015 | Nair et al. |
| 2015/0213222 A1 | 7/2015 | Amarasingham et al. |
| 2015/0213379 A1 | 7/2015 | Nair et al. |
| 2015/0216369 A1 | 8/2015 | Hamilton et al. |
| 2015/0253748 A1 | 9/2015 | Brun et al. |
| 2015/0281287 A1 | 10/2015 | Gill et al. |
| 2015/0310312 A1 | 10/2015 | Mongeon et al. |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0063833 A1 | 3/2016 | Schultz et al. |
| 2016/0066067 A1 | 3/2016 | Schultz et al. |
| 2016/0110833 A1 | 4/2016 | Fix et al. |
| 2016/0116181 A1 | 4/2016 | Aultman et al. |
| 2016/0139067 A1 | 5/2016 | Grace |
| 2016/0253897 A1 | 9/2016 | Wildman et al. |
| 2016/0255516 A1 | 9/2016 | Hill et al. |
| 2016/0298864 A1 | 10/2016 | Ekolind et al. |
| 2016/0306934 A1 | 10/2016 | Sperry et al. |
| 2016/0314683 A1 | 10/2016 | Felch et al. |
| 2016/0328948 A1 | 11/2016 | Ferniany |
| 2016/0335731 A1 | 11/2016 | Hall |
| 2016/0367925 A1 | 12/2016 | Blackley |
| 2016/0371619 A1 | 12/2016 | Foster |
| 2017/0024986 A1 | 1/2017 | Austin |
| 2017/0193792 A1 | 7/2017 | Bermudez Rodriguez et al. |
| 2017/0256155 A1 | 9/2017 | Sengstaken, Jr. |
| 2017/0280949 A1 | 10/2017 | Wildman et al. |
| 2017/0294106 A1 | 10/2017 | Thyroff |
| 2017/0365024 A1 | 12/2017 | Koch et al. |
| 2018/0004178 A1 | 1/2018 | Haines et al. |
| 2018/0016773 A1 | 1/2018 | Chandler et al. |
| 2018/0113897 A1 | 4/2018 | Donlan et al. |
| 2018/0151054 A1 | 5/2018 | Pi |
| 2018/0218591 A1 | 8/2018 | Easter |
| 2018/0293038 A1 | 10/2018 | Meruva et al. |
| 2018/0301014 A1 | 10/2018 | Worral et al. |
| 2018/0313695 A1 | 11/2018 | Shim et al. |
| 2018/0365957 A1 | 12/2018 | Wright et al. |
| 2019/0012607 A1 | 1/2019 | Holliday et al. |
| 2019/0051138 A1 | 2/2019 | Easter |
| 2019/0139395 A1 | 5/2019 | Rogachev et al. |
| 2019/0209719 A1 | 7/2019 | Andersen et al. |
| 2019/0295386 A1 | 9/2019 | Roberts |
| 2020/0009280 A1 | 1/2020 | Kupa et al. |
| 2020/0074836 A1 | 3/2020 | Kolavennu et al. |
| 2020/0090089 A1 | 3/2020 | Aston et al. |
| 2020/0146557 A1 | 5/2020 | Cheung et al. |
| 2020/0200420 A1 | 6/2020 | Nayak et al. |
| 2020/0224915 A1* | 7/2020 | Nourbakhsh ............ F24F 11/54 |
| 2020/0327315 A1 | 10/2020 | Mullins |
| 2020/0348038 A1* | 11/2020 | Risbeck .................. F24F 11/70 |
| 2020/0364999 A1 | 11/2020 | Mullins |
| 2021/0311055 A1* | 10/2021 | McDevitt ............. G01N 33/548 |
| 2022/0058556 A1* | 2/2022 | Warake ............ G05B 19/41855 |

FOREIGN PATENT DOCUMENTS

| | | |
|---|---|---|
| CN | 103110410 A | 5/2013 |
| CN | 103970977 A | 8/2014 |
| CN | 105116848 A | 12/2015 |
| CN | 108961714 A | 12/2018 |
| CN | 110009245 A | 7/2019 |
| CN | 110084928 A | 8/2019 |
| CN | 110827457 A | 2/2020 |
| EP | 1669912 A1 | 6/2006 |
| EP | 2310981 A1 | 4/2011 |
| JP | 7085166 A | 3/1995 |
| JP | 11024735 A | 1/1999 |
| JP | 11317936 A | 11/1999 |
| JP | 2001356813 A | 12/2001 |
| JP | 2005242531 A | 9/2005 |
| JP | 2005311563 A | 11/2005 |
| KR | 1172747 B1 | 8/2012 |
| KR | 101445367 B1 | 10/2014 |
| KR | 1499081 B1 | 3/2015 |
| WO | 9621264 A3 | 11/1996 |
| WO | 2004029518 A1 | 4/2004 |
| WO | 2005045715 A2 | 5/2005 |
| WO | 2008152433 A1 | 12/2008 |
| WO | 2008157755 A1 | 12/2008 |
| WO | 2009012319 A2 | 1/2009 |
| WO | 2009079648 A1 | 6/2009 |
| WO | 2010106474 A1 | 9/2010 |
| WO | 2011025085 A1 | 3/2011 |
| WO | 2011043732 A1 | 4/2011 |
| WO | 2011057173 A2 | 5/2011 |

(56) References Cited

FOREIGN PATENT DOCUMENTS

| | | |
|---|---|---|
| WO | 2011123743 A1 | 10/2011 |
| WO | 2013062725 A1 | 5/2013 |
| WO | 2013178819 A1 | 12/2013 |
| WO | 2014009291 A1 | 1/2014 |
| WO | 2014098861 A1 | 6/2014 |
| WO | 2014135517 A1 | 9/2014 |
| WO | 2016123536 A1 | 8/2016 |
| WO | 2017057274 A1 | 4/2017 |
| WO | 2019046580 A1 | 3/2019 |
| WO | 2020024553 A1 | 2/2020 |

OTHER PUBLICATIONS

Shhedi et al., "Traditional and ICT Solutions for Preventing the Hospital Acquired Infection", 2015 20th International Conference on Control Systems and Computer Science, IEEE, May 27, 2015, pp. 867-873, XP033188038.
Extended European Search Report, EP application No. 20151295.1, pp. 13, May 26, 2020.
U.S. Appl. No. 14/109,496, filed Dec. 17, 2013.
"What is the GE Nucleus Home Manager? How can a Home Manager Help with Energy Conservation?" GE Nucleus, 2 pages, printed Jan. 15, 2013. www.geappliances.com/home-energy-manager/about-energy-monitors.htm.
"Lucid Design Group—Building Dashboard Network—Apps," 7 pages, Jan. 15, 2013. www.luciddesigngroup.com/network/apps.php#homepage.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.
"The Home Dashboard," CRBM info@hand website, 46 pages, prior to Apr. 25, 2013.
"Free Facilities Dashboards," eSight Energy Website, 2 pages, prior to Apr. 25, 2013.
Alerton Building Controls, Gallery Prints, 7 pages, Dec. 19, 2013.
Carter, "Industrial Energy Management Dashboards Require a Toolkit," Cross Automation, 11 pages, Nov. 4, 2013.
U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
e-homecontrols.com, "e-Home Controls Website," link to actual website no longer works, 1 page, prior to Dec. 19, 2013.
"C&C (/)—Omniboard," 5 pages, Dec. 19, 2013. http://www.ccbac.com.
"DomController Home Automation Software—Control Anything from Anywhere," 11 pages, printed Jan. 6, 2015. http://www.domcontroller.com/en/.
"Novar OPUS BAS," 1 page, prior to Feb. 13, 2013. http://www.novar.com/ems-bas/opus-building-automation-system.
"A 3D Interactive Environment for Automated Building Control," Master's Dissertation, Instituto Superior Tecnico, 120 pages, Nov. 2012.
Panduit Corp., "Enable a Building Automation with Panduit Enterprise Solutions," 4 pages, Nov. 2012.
Honeywell, "WEBs-AX Web-Enabled Building Solutions," sales brochure, Honeywell International Inc., Mar. 2009.
Honeywell, "Attune Advisory Services," press release, Honeywell International Inc., Mar. 20, 2012.
EnteliWEB Overview, web pages retrieved on May 9, 2013 from http://deltacontrols.com/products/facilities-management/supervisory-software et seq. by the Internet Archive at web.archive.org.
"BACnet Protocol Implementation Conformance Statement" for enteliWEB, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWEB "Software: Enterprise Energy Management", catalog sheet, Delta Controls, 2012.
EnteliWEB "Software: Enterprise Energy Management", catalog sheet, Delta Controls., 2010.
"Intelligent Building Management Systems in Miami," Advanced Control Corp., Mar. 7, 2013.
"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," Aug. 28, 2013, https://www.greenbiz.com/blog/2013/08/28/9-key-attributes-energy-dashboards-and=analytics-tools.
Sinopoli, "Dashboards for Buildings," http://www/automatedbuildings.com/news/dec10/articles/sinopoli/101119034404sinopoli.html, Dec. 2010.
Sinopoli, "Modeling Building Automation and Control Systems," http://www.automatedbuildings.com/news/jun13/articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
International Search Report and Written Opinion dated Jul. 17, 2018 for International PCT Application No. PCT/US2018/025189 (12 pages).
"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.
Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.
"ASHRAE Dashboard Research Project," 29 pages, Aug. 28, 2008.
Honeywell, "Energy Manager User Guide," Release 3.2, 180 pages, 2008.
"Fuzzy Logic Toolbox 2.1, Design and Stimulate Fuzzy Logic Systems," The MathWorks, 2 pages, May 2004.
"Junk Charts, Recycling Chartjunk as junk art," 3 pages, Oct. 2, 2006.
"Model Predictive Control Toolbox 2, Develop Internal Model-Based Controllers for Constrained Multivariable Processes," The MathWorks, 4 pages, Mar. 2005.
Honeywell, "Product Guide 2004," XP-002472407, 127 pages, 2004.
"Statistics Toolbox, for Use with Matlab," User's Guide Version2, The MathWorks, 408 pages, Jan. 1999.
"Vykon Energy Suite Student Guide," Tridium Inc., 307 pages, Mar. 3, 2006.
"Web Based Energy Information Systems for Energy Management and Demand Response in Commercial Buildings," California Energy Commission, 80 pages, Oct. 2003.

(56) References Cited

OTHER PUBLICATIONS

Andover Controls, Network News, vol. 2, No. 2, 8 pages, 1997.
Andover Controls World, 4 pages, Spring 1997.
Bell et al., "Early Event Detection—Results from a Prototype Implementation," AICHE Spring National Meeting, 15 pages, Apr. 2005.
Cadgraphics, "The Cadgraphics User's Guide," 198 pages, 2003.
Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chan, "Rank Revealing QR Factorizations," Linear Algebra and It's Applications, vol. 88-89, p. 67-82, Apr. 1987.
Circon, "i-Browse Web-Based Monitoring and Control for Facility Management," 2 pages, prior to Aug. 27, 2007.
Australian Application 2009904740, Published copy, 28 pages, Application Filed on Sep. 29, 2009.
Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . . " 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.
Honeywell, "Excel Building Supervisor-Integrated R7044 and FS90 Ver. 2.0," Operator Manual, 70 pages, Apr. 1995.
Honeywell Home and Building Control Bulletin, "Introduction of the S7350A Honeywell WebPad Information Appliance," 2 pages, Aug. 29, 2000; Picture of WebPad Device with touch screen, 1 Page; and screen shots of WebPad Device, 4 pages.
Honeywell, Excel 15B W7760B Building Manager Release Feb. 2, 2000, Installation Instructions, 28 pages, Dec. 2004.
Honeywell, The RapidZone Solution, Excel 5000 Open System, Application Guide, 52 pages, Jan. 2004.
"Remote Building Monitoring and Operations Home Page," 5 pages, prior to Aug. 27, 2007.
"Carrier: i-Vu CCN," 1 page, printed Mar. 11, 2008.
Carrier: 33CSCCNWeb-01 CCM Web Internet Connection to the Carrier Comfort Network, 1 page, printed Mar. 11, 2008.
"Products," 5 pages, printed Jul. 3, 2007. http://www.docs.hvacpartners.com/idc/groups/public/documents/techlit/gs-controls-ivuccn.rtf.
Lightstat Incorporated, "Internet Programmable Communicating Thermostats," 1 page, printed Mar. 13, 2007. http://www.lightstat.com/products/istat.asp.
Sharp, "Actius RD3D Desktop Replacement Notebook with Industry-Breakthrough 3D Screen," 1 page, printed Jun. 16, 2005. http://www.sharpsystems.com/products/pc_notebooks/actius/rd/3d/.
"Lights on a Wireless Lighting Control System," 11 pages, printed Mar. 22, 2007 http://www2.sims.berkeley.edu/courses/is213/s06/projects/lightson;final.html.
I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Ball, "Green Goal of 'Carbon Neutrality' Hits Limit," TheWall Street Journal, 7 pages, Dec. 30, 2008.

Network Integration Engine (NIE), Johnson Controls, 3 pages, Nov. 9, 2007.
Network Integration Engine (NIE), Product Bulletin, Johnson Controls, pp. 1-11, Jan. 30, 2008.
Kourti, "Process Analysis and Abnormal Situation Detection: From Theory to Practice," IEEE Control Systems Magazine, p. 10-25, Oct. 2002.
Mathew, "Action-Oriented Benchmarking, Using CEUS Date to Identify and Prioritize Efficiency Opportunities in California Commercial Buildings," 26 pages, Jun. 2007.
Morrison et al., "The Early Event Detection Toolkit," Honeywell Process Solutions, 14 pages, Jan. 2006.
Narang, "WEBARC: Control and Monitoring of Building Systems Over the Web," 53 pages, May 1999.
Olken et al., "Object Lessons Learned from a Distributed System for Remote Building Monitoring and Operation," ACM SIGPLAN Notices, vol. 33, No. 10, pp. 284-295, Oct. 1998.
Proliphix, Inc., "Proliphix IP Devices: HTTP API," 28 pages, Jan. 23, 2006.
Proliphix, Inc., "Remote Management User Guide," 12 pages, prior to Aug. 27, 2007.
Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," ASHRAE Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam Ltd, 11 pages, Jun. 5, 2020.
"Thermal Imaging SmartPhone Can Be used for Temperature Screening of People," CAT, 3 pages, accessed Jul. 13, 2020.
"Contact Tracing Now Available on Identiv's Hirsch Velocity Access Control Platform," Identiv, 5 pages, May 21, 2020.
Silva et al., "Cough localization for the detection of respiratory diseases in pig houses," ScienceDirect, 7 pages, May 28, 2008.
Oey et al., "Evaluation of Isolation Compliance Using Real Time Video in Critical Care," North Shore University Hospital, 1 page, Oct. 9, 2015.
"Facial Attendace System With Temperature Screening Now in India," IANS, 5 pages, Mar. 19, 2020.
"Plan to Re-Open," EHIGH, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
Honeywell, "Inncontrol 5," 2 pages, Aug. 8, 2018.
"IP Door Access Control," Kintronics, 21 pages, 2014.
"Kogniz AI Health Response Platform," Kogniz, 9 pages, accessed May 21, 2020.
"Machine Learning Could Check If You're Social Distancing Properly at Work," MIT Technology Review, 7 pages, Apr. 17, 2020.
Punn et al., "Monitoring COVID-19 social distancing with person detection and tracking via fine-tuned YOLO v3 and Deepsort techniques," 10 pages, May 6, 2020.

(56) References Cited

OTHER PUBLICATIONS

Burt, "NEC launches dual face biometric and fever detection system for access control," Biometric Update, 4 pages, May 8, 2020.
"Remote temperature monitoring," AXIS Communication, 10 pages, 2014.
"FebriEye—AI Based Thermal Temperature Screening System," vehant, 1 page, 2020.
"See the World in a New Way Hikvision Thermal Cameras," Hikvision, 12 pages, 2017.
Allain, "Trying out the iPhone Infrared Camera: The FLIR One," Wired, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered JARVIS to battle coronavirus," Yourstory, 7 pages, Mar. 31, 2020.
Trane, "Creating Input/Output Objects," 196 pages, retrieved Jul. 10, 2020.
Trane, "Using the Graphing Control Editor," 181 pages, retrieved Jul. 10, 2020.
Genetec, Feature note, "Dashboards, A comprehensive view of your security and operations", pp. 2, 2019 Genetec Inc.
U.S. Appl. No. 16/907,018, filed Jun. 19, 2020.
U.S. Appl. No. 16/907,044, filed Jun. 19, 2020.
U.S. Appl. No. 16/922,693, filed Jul. 7, 2020.
U.S. Appl. No. 17/141,844, filed Jan. 5, 2021.
U.S. Appl. No. 17/314,565, filed Jun. 22, 2020.

\* cited by examiner

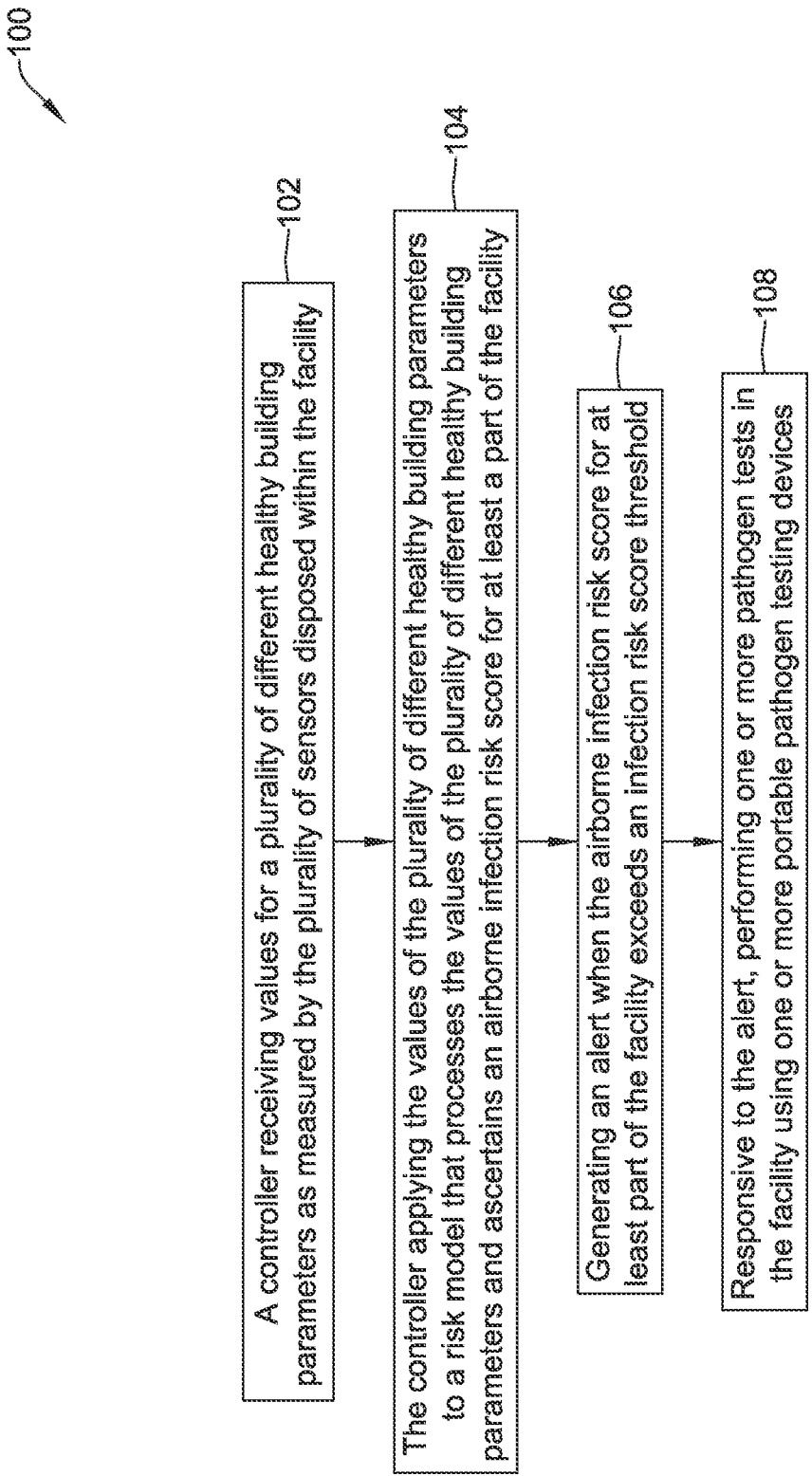

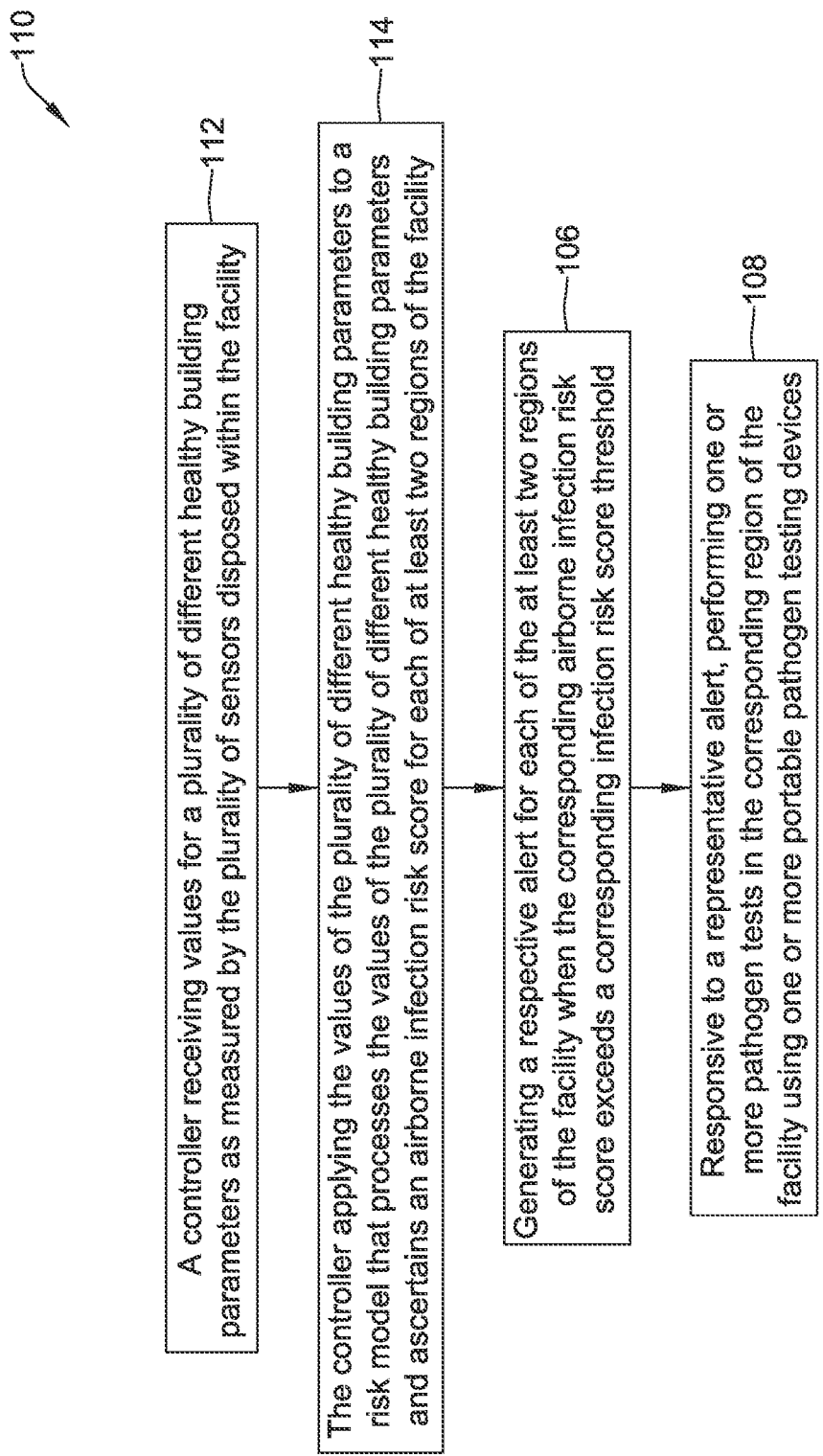

```
                    ┌─ 122
                    │
    ┌───────────────────────────────┐
    │ A controller receiving values for a plurality of different healthy building │
    │ parameters as measured by the plurality of sensors disposed within the facility │
    └───────────────────────────────┘
                    │
                    ▼
    ┌─────────────────────────────────── 124
    │ The controller applying the values of the plurality of different healthy building parameters
    │ to a risk model that processes the values of the plurality of different healthy building
    │ parameters and ascertains an airborne infection risk score for each of at least two
    │ regions of the facility and also ascertains an overall airborne infection risk score for the
    │ facility, wherein the overall airborne infection risk score for the facility is dependent on
    │ the airborne infection risk score for each of the at least two regions of the facility
    └───────────────────────────────────
                    │
                    ▼
    ┌─── 126
    │ Displaying the overall airborne infection risk score for the facility on a dashboard │
    └───
                    │
                    ▼
    ┌─── 128
    │ From the dashboard, accepting an input from a user, wherein responsive
    │ to receiving the input from the user, displaying the airborne infection risk
    │ score for one or more of the at least two regions of the facility
    └───
```

FIG. 9

AIRBORNE INFECTION EARLY WARNING SYSTEM

TECHNICAL FIELD

The present disclosure pertains to protecting against airborne infections. More particularly, the present disclosure pertains to providing an early warning system pertaining to risks of airborne infections.

BACKGROUND

A variety of infectious diseases are transmitted via airborne and/or other particles. In some cases, it may be difficult to mitigate the spread of infectious diseases, particularly diseases transmitted through airborne and/or other particles, at indoor facilities (e.g., buildings, department stores, warehouses, plants, factories, refineries, airports, laboratories, school buildings, theaters, etc.) due to the indoor environment, proximity of occupants, and/or other factors. Often, these indoor facilities have various building automation systems (e.g., heating, ventilation, and air conditioning (HVAC) systems, surveillance systems, security systems, energy management systems, etc.) to control environmental conditions of the indoor facility and/or monitor occupancy. A need remains for ways to protect against airborne infections, including providing an early warning system.

SUMMARY

The present disclosure relates to protecting against airborne infections. In an example, a method provides for reducing risks of airborne infection within a facility having a Building Management System (BMS) with a plurality of sensors disposed within the facility configured to measure a plurality of different healthy building parameters that impact risk of airborne infection. The method includes a controller receiving values for a plurality of different healthy building parameters as measured by the plurality of sensors disposed within the facility. The controller applies the values of the plurality of different healthy building parameters to a risk model that processes the values of the plurality of different healthy building parameters in order to ascertain an airborne infection risk score for at least part of the facility and one or more suggested changes to a current operation of the BMS system in order to reduce the airborne infection risk score. Suggested changes to the current operation of the BMS system may include, for example, modifying one or more settings of existing equipment, upgrading existing equipment, adding new equipment, and/or any other suitable changes. In some cases, one or more operational commands are provided to the BMS system in order to implement one or more of the suggested changes to the current operation of the BMS system.

In another example, a method provides for reducing risks of airborne infection within a facility having a Building Management System (BMS) with a plurality of sensors disposed within the facility configured to measure a plurality of different healthy building parameters that impact risk of airborne infection. The method includes a controller receiving values for a plurality of different healthy building parameters as measured by the plurality of sensors disposed within the facility. The controller applies the values of the plurality of different healthy building parameters to a risk model that processes the values of the plurality of different healthy building parameters and ascertains an airborne infection risk score for at least part of the facility. An alert is generated when the airborne infection risk score for at least part of the facility exceeds an infection risk score threshold. In response to the alert, one or more pathogen tests may be ordered up and performed using one or more portable pathogen testing devices.

In another example, a method provides for identifying risks of airborne infection within a facility having a Building Management System (BMS) with a plurality of sensors disposed within the facility configured to measure a plurality of different healthy building parameters that impact risk of airborne infection. The illustrative method includes a controller receiving values for a plurality of different healthy building parameters as measured by the plurality of sensors disposed within the facility. The controller applies the values of the plurality of different healthy building parameters to a risk model that processes the values of the plurality of different healthy building parameters and ascertains an airborne infection risk score for each of at least two regions of the facility and also ascertains an overall airborne infection risk score for the facility, wherein the overall airborne infection risk score for the facility is dependent on the airborne infection risk scores for each of the at least two regions of the facility. The overall airborne infection risk score for the facility is displayed on a dashboard. From the dashboard, an input is accepted from a user. Responsive to receiving the input from the user, the airborne infection risk score for one or more of the at least two regions of the facility is displayed.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments of the disclosure in connection with the accompanying drawings, in which:

FIG. 7 is a flow diagram showing an illustrative method;
FIG. 8 is a flow diagram showing an illustrative method;
and
FIG. 9 is a flow diagram showing an illustrative method.

Figure 1:
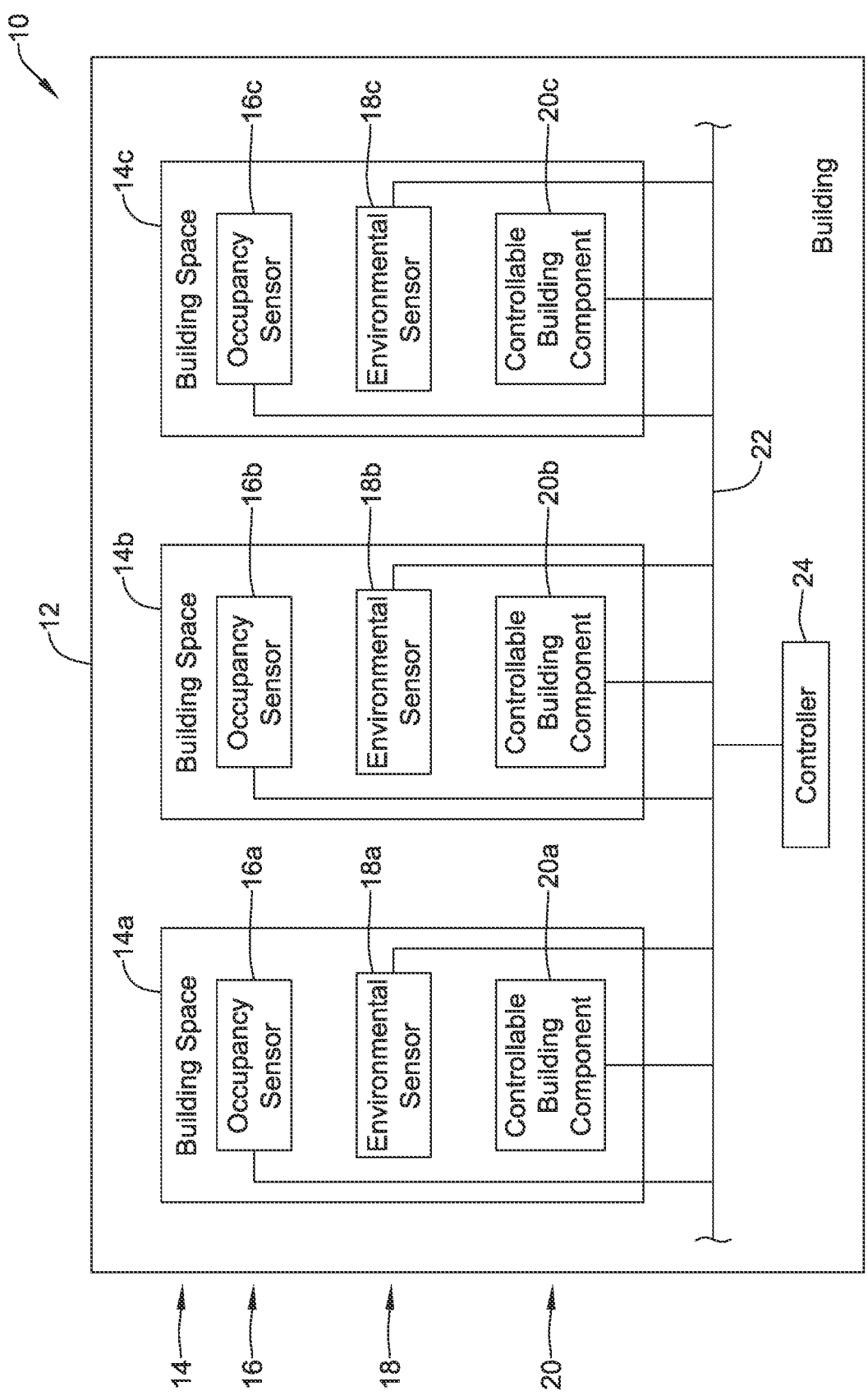
FIG. 1 is a schematic block diagram of an illustrative building management system.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings wherein like reference numerals indicate like elements. The drawings, which are not necessarily to scale, are not intended to limit the scope of the disclosure. In some of the figures, elements not believed necessary to an understanding of relationships among illustrated components may have been omitted for clarity.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

Facilities often include building automation systems (e.g., heating, ventilation, and air conditioning (HVAC) systems, surveillance systems, security systems, energy management systems, etc.). Various organizations worldwide (e.g., government organizations, educational organizations, etc.) have provided guidelines on how to operate building automation system to reduce risk of disease transmissions within facilities. Similarly, various organizations worldwide have provided guidelines on how occupants of a facility and monitoring occupancy can reduced risk of disease transmission. Other guidelines relating to facilities and transmission of infectious disease are contemplated and may be adapted and used, depending on the facility.

FIG. 1 is a schematic block diagram of an illustrative building management system 10. The illustrative building management system 10 is installed in a building 12 and may be considered as being configured to reduce the risk of pathogenic exposure within the building 12. The building 12 includes a number of building spaces 14 that are individually labeled as 14a, 14b, 14c. It will be appreciated that this is merely illustrative, as the building 12 will typically include a much greater number of building spaces 14 or zones. At least some of the building spaces 14 may periodically have one or more people within the building space 14. In some cases, the building 12 may be a hotel, and thus the building spaces 14 may be individually rentable guest rooms. The building 12 may be an office building, or a portion of an office building, and thus the building spaces 14 may be individual offices or work spaces. In some case, the disclosure may be applied to a cruise ship. These are just examples.

In the example shown, each of the building spaces 14 includes one or more occupancy sensors 16, although only one occupancy sensor 16 is shown in each of the building spaces 14. The occupancy sensors 16 are individually labeled as 16a, 16b, 16c. When provided, at least some of the occupancy sensors 16 may be PIR sensors, mmWave sensors, motion sensors and/or microphones, for example. Some of the occupancy sensors 16 may be part of a security system of the building 12, for example. In some cases, some of the occupancy sensors 16 may be video cameras that are coupled with video analytics to detect the presence of one or more people, and hence determine occupancy. Occupancy detection may include detecting the presence of people, including counting people. Occupancy detection may also include behavioral indicators such as hand washing, signs of illness such as fever and coughing, spacing between people, mask compliance, and the like.

In the example shown, each of the building spaces 14 also include one or more environmental sensors 18, although only one environmental sensor 18 is shown in each of the building spaces 14. The environmental sensors 18 are individually labeled as 18a, 18b, 18c. The environmental sensors 18 may, for example, include sensors such as temperature sensors, humidity sensors, visible light sensors, UV sensors, particulate matter sensors (e.g. PM2.5, PM10), VOC sensors, airborne and waterborne pathogen sensors, CO sensors, CO2 sensors, ozone sensors, and/or any other environmental suitable sensor. In some cases, some of the environmental sensors 18 may be considered as being Indoor Air Quality (IAQ) sensors. In some cases, one or more of the environmental sensors 18 may be disposed within a room thermostat within at least some of the building spaces 14.

In some cases, sensing environmental parameters may include sensing air pressure in general, and air pressure differentials across the building 12 in particular. It has been found that air pressure differentials can provide a general indication of air flow through the building 12. Air will flow from an area of higher pressure to an area of lower pressure, for example. Measuring air pressure differentials can also provide an indication of how opening and closing windows and doors can influence air flow through the building 12, for example. Measuring air pressure differentials can also provide an indication of the impact of turning ventilation on or off, or turning ventilation rates up and down, among other HVAC capabilities. In some cases, controlled air flow is one of the key techniques highlighted by ASHRAE (American Society of Heating, Refrigerating and Air Conditioning Engineers) to control airborne pathogen transmission.

If a building space 14 is in a hospital operating room, for example, there is typically a desire to maintain an air pressure within the operating room that is higher than the air pressure in neighboring spaces. This can help to limit airborne pathogens from entering the operating room, as any air movement will tend to be from inside the operating room to outside of the operating room. If a building space 14 is not occupied, there may be a desire to reduce air flow in the duct(s) that provide conditioned air to the building space 14 in order to, for example, increase an amount of time that any airborne pathogens are exposed to UV light during a sanitizing process of the unoccupied room. These are just examples.

In the example shown, each of the building spaces 14 includes one or more controllable building components 20, although only one controllable building component 20 is shown in each of the building spaces 14. Each of the controllable building components 20 may be considered as being configured to control environmental conditions within the building spaces 14 in order to reduce the likelihood of disease transmission among occupants of the building 12. At least some of the controllable building components 20 may include heating, ventilating and air conditioning system (HVAC) components such as heating sources, cooling sources, ventilation sources, humidifiers and dehumidifiers, as examples. At least some of the controllable building components 20 may include a disinfecting component. Examples of disinfecting components include sources of UV light that may be used to sanitize surfaces within the building space 14. UV light sources may also be used to disinfect components of an HVAC system, such as but not limited to disinfecting filters within the HVAC system. This may include cleaning filter media as well as electrostatic filters.

The UV light spectrum ranges from about 100 nanometers (nm) to about 400 nm. The UV light spectrum includes UV-A, which ranges from 315 nm to 400 nm. This UV light spectrum also includes UV-B, which ranges from 280 nm to 315 nm. UV-C, which ranges from 200 nm to 280 nm, is particularly effective for disinfecting. There is also Far-UVC, which ranges from 207 nm to 222 nm and thus is a subset of the UV-C light spectrum. Far-UVC is also particularly effective for disinfecting, and is believed to be safe for human skin and eyes. The UV light spectrum also includes VUV Far-UV, which ranges from 100 nm to 200 nm. In some cases, at least some of the controllable building components 20 may include a source of UV-C light that is configured to provide UV-C light for a period of time sufficient to disinfect surfaces within the building space 14. For example, it may take a period of time, such as 5 minutes, 10 minutes, 30 minutes, 1 hour, 2 hours, 3 hours or more, depending on a number of factors such as the intensity of the UV-C light source and the distance between the UV-C light source and the surfaces to be sanitized.

In the example shown, each of the occupancy sensors 16, each of the environmental sensors 18 and each of the controllable building components 20 are operably coupled with a building network 22. A controller 24 is operably coupled with the building network 22 such that the controller 24 is able to receive occupancy data from the occupancy sensors 16 and indoor air quality data from the environmental sensors 18. Accordingly, each of the one or more occupancy sensors 16 may be considered as providing occupancy signals over the building network 22. Similarly, each of the one or more environmental sensors 18 may be considered as providing air quality parameter signals over the building network 22. In some cases, the one or more environmental sensors 18 may provide a measurement of carbon dioxide concentration as a basic occupancy indicator. It will be appreciated that carbon dioxide concentration will increase as additional people are present within the building space 14, and will decrease as people leave the building space 14.

The controller 24 is also able to provide control signals to the controllable building components 20 via the building network 22. It is contemplated that the building network 22 may be a wired network, a wireless network or a combination of wired and wireless. It will be appreciated that while the controller 24 is shown as being located inside of the building 12, this is not required in all cases. In some instances, the controller 24 may itself be manifested within one or more computing devices that may be local to the building 12 or may be remote from the building 12. In some case, all or part of the controller 24 may be manifested within a cloud-based server.

In some instances, the controller 24 is configured to receive occupancy signals from the one or more occupancy sensors 16 over the building network 22 and to receive indoor air quality parameter signals from the one or more environmental sensors 18 over the building network 22. The controller 24 is configured to process the received occupancy signals and the received indoor air quality parameter signals (sometimes in combination) to determine whether action is needed to improve one or more environmental conditions within at least some of the plurality of building spaces 14 in order to reduce the likelihood of disease transmission among occupants of the building 12. Responsive to determining that action is needed, the controller 24 is configured to send control signals to one or more of controllable building components over the building network to improve one or more environmental conditions within at least some of the plurality of building spaces to reduce the likelihood of disease transmission among occupants of the building.

Figure 2:
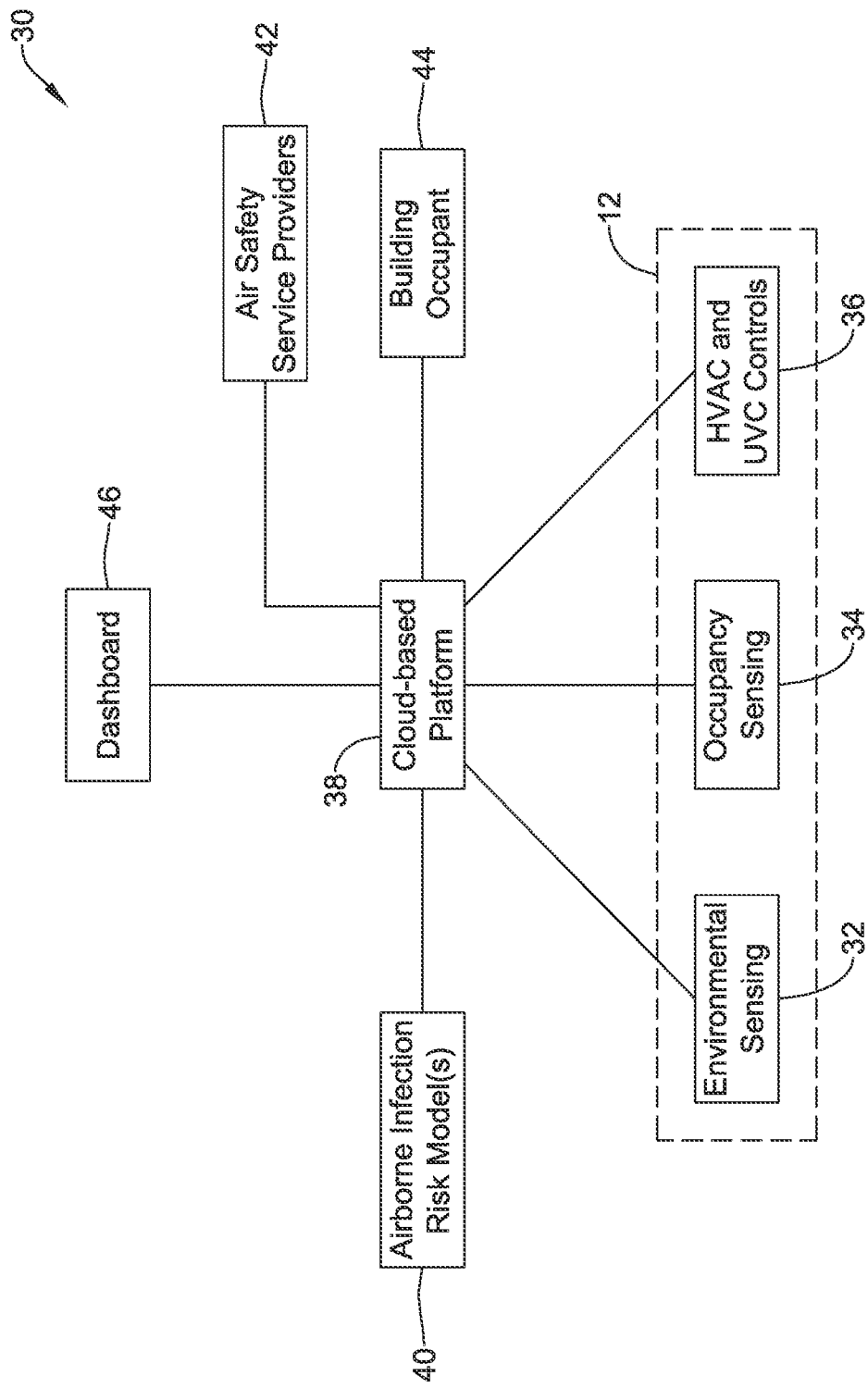
FIG. 2 is a schematic block diagram of an illustrative monitoring system.

FIG. 2 is a schematic block diagram of an illustrative monitoring system 30 that may be utilized by a controller, such as controller 24 (FIG. 1). In some cases, the controller 24 may utilize the monitoring system 30 to ascertain current risks of airborne infections within the building 12 (or within individual spaces 14 of the building 12), based on current parameter values provided by the occupancy sensors 16 and/or the environmental sensors 18, for example. The monitoring system 30 may be considered as providing additional functionality to the controller 24. In some instances, the monitoring system 30 may be in communication with a plurality of different controllers 24, each within a separate building 12.

The illustrative monitoring system 30 includes an environmental sensing block 32 and an occupancy sensing 34 block. The environmental sensing block 32 may, for example, be considered as being representative of the environmental sensors 18 within a particular building 12. The occupancy sensing block 34 may, for example, be considered as being representative of the occupancy sensors 16 within a particular building 12. The illustrative monitoring system 30 includes an HVAC and UVC controls block 36. The HVAC and UVC controls block 36 may be considered as representing the addressable controls over the controllable building components 20 (FIG. 1). It is contemplated that the various blocks 32, 34 and 36 shown in FIG. 2 are only illustrative, and that more, less or different blocks may be used, as desired.

In the example shown, the environmental sensing block 32, the occupancy sensing block 34 and the HVAC and UVC controls block 36 may be considered as being operably coupled with a cloud-based platform 38. The cloud-based platform 38 may represent one or more cloud-based servers, for example, and may be configured to receive data from the environmental sensing block 32 and the occupancy sensing block 34 and to provide appropriate commands to the HVAC and UVC controls block 36 in order to provide control (sometimes closed loop control) over the controllable building components within the building 12 in order to maintain and/or improve conditions inside the building 12, including but not limited to meeting healthy building guidelines and otherwise reducing the risk of airborne infections. Honeywell Forge™ is an example of the cloud-based platform 38.

In some instances, the cloud-based platform 38 communicates with an Airborne Infection Risk Model block 40. While shown as a separate block, it is contemplated that in some instances the Airborne Infection Risk Model block 40 may be manifested within the cloud-based platform 38. In some cases, the Airborne Infection Risk Model block 40 may be present on a separate server that is in communication with the cloud-based platform 38 and thus is indirectly in communication with the building level environmental sensing block 32, the occupancy sensing block 34 and the HVAC and UVC controls block 36. In some cases, the Airborne Infection Risk model block 40 may include or reference one or more proprietary risk models that are disposed within a remote server. Illustrative but non-limiting examples include dynamic risk models such as those available commercially from RESET as well as static models such as a spreadsheet-based risk model available from the University of Colorado at Boulder.

In some cases, the cloud-based platform 38 receives data representing a number of healthy building parameters from the environmental sensing block 32 and the occupancy sensing block 34, and provides this data to the Airborne Infection Risk model block 40. In turn, the Airborne Infection Risk model block 40 processes the data and provides back to the cloud-based platform 38 a corresponding airborne infection risk score for a particular part of a building 12, and in some cases one or more suggested changes to current operation of the building 12 in order to lessen the risk of airborne infection. In some cases, the cloud-based platform 38 determines one or more suggested changes to current operation of the building 12 in order to lessen the risk of airborne infection. The cloud-based platform 38 then provides this information back to the particular building 12, such as to the controller 24 within the particular building 12.

The risk model(s) available within the Airborne Infection Risk model block 40 may be configured to provide a building level index that indicates an overall infection risk for a building or other facility overall. In some cases, depending on the data made available to the risk model(s), the risk model(s) may be configured to drill down within the building or facility, and provide an indication of an infection risk for particular zones or spaces within the building or facility. In some cases, the risk model(s) may be utilized by the cloud-based platform 38 to execute what-if scenarios such as exploring which of several different conference rooms may be safest to use for a particularly-sized group of people, for example. Another example of a what-if scenario that may be executed includes exploring how the infection risk index for a particular space may vary, depending on various HVAC system settings, for example, relative to varying outdoor conditions such as outdoor temperature and outdoor humidity. It will be appreciated that if the outdoor air is unusually cold and dry, this may impact feasible ventilation rates, which in turn could impact feasible occupancy levels and costs. These are just examples.

The cloud-based platform 38 may communicate with an Air Safety Service Providers block 42. In some cases, the Air Safety Service Providers block 42 may provide the cloud-based platform 38 with information pertaining to various testing equipment that may be deployed within the building or facility 12 in order to test for and thus detect the presence of actual bacteria and/or viruses. The Air Safety Service Providers block 42 may also provide the cloud-based platform 38 with information pertaining to filtration and other technologies that may be used to reduce the presence of actual bacterial and/or viruses within the building or facility 12. In some cases, the cloud-based platform 38 may, through a Building Occupant block 44, recommend the use of various services available through the Air Safety Service Providers block 42.

The Building Occupant block 44 may be used by the cloud-based platform 38 to communicate with a building or facility manager within the building or facility 12. An example might be the cloud-based platform 38 recommending that for a particular group of people desiring to meet at a particular day and time, that a particular conference room may be a safer choice than a different conference room. This recommendation may, for example, be based on how recently the various conference rooms hosted a large group of people, or how recently each of the various conference rooms has undergone a deep cleaning. The recommendation may be based at least in part upon known idiosyncrasies of the building's HVAC and/or ventilation systems, for example.

The illustrative monitoring system 30 also includes a Dashboard block 46. The cloud-based platform 38 may provide various data to the Dashboard block 46, which in turn may be configured to generate and display one or more dashboards in order to provide information to the building or facility manager in an easy to read manner. The Dashboard block 46, which may be distinct from the cloud-based platform 38 or may be manifested within the cloud-based platform 38, may display the results of various analytics that were performed by the cloud-based platform 38. This may include displaying a risk infection score determined by the cloud-based platform 38 in conjunction with the Airborne Infection Risk Model block 40, for example.

Figure 3:
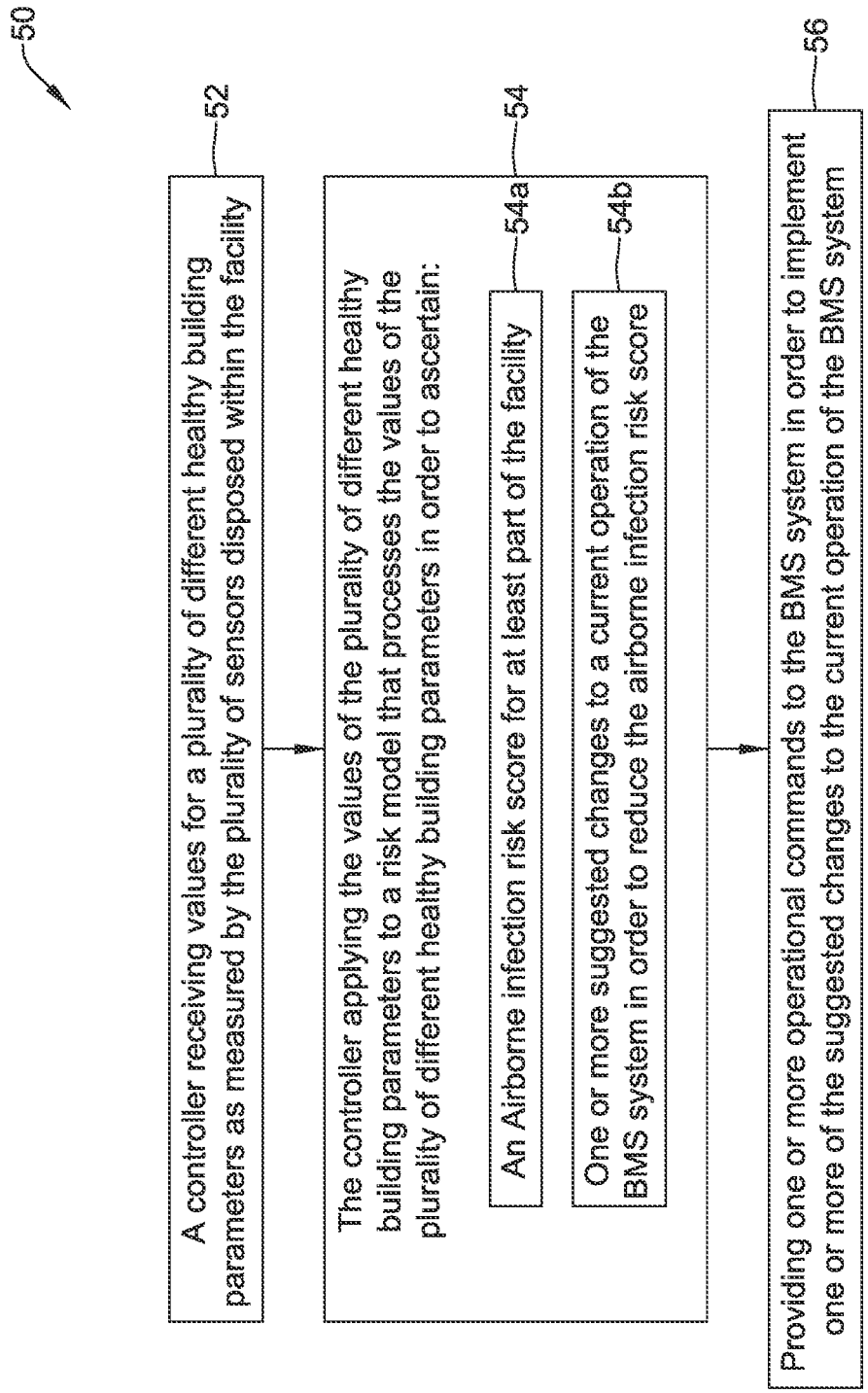
FIG. 3 is a flow diagram showing an illustrative method.

FIG. 3 is a flow diagram showing an illustrative method 50 for reducing risks of airborne infection within a facility having a Building Management System (BMS) with a plurality of sensors disposed within the facility configured to measure a plurality of different healthy building parameters that impact risk of airborne infection. The plurality of sensors may include a temperature sensor and a humidity sensor. The plurality of sensors may further include a particulate matter sensor and/or a total volatile organic compounds sensor. The plurality of sensors may further include a CO sensor and/or an occupancy sensor. In some cases, the plurality of sensors may further include a video camera.

The method 50 includes a controller (such as the controller 24) receiving values for a plurality of different healthy building parameters as measured by the plurality of sensors disposed within the facility, as indicated at block 52. The controller applies the values of the plurality of different healthy building parameters to a risk model that processes the values of the plurality of different healthy building parameters, as indicated at block 54. In some cases, this may include tracking the values of at least some of the plurality of different healthy building parameters over time in order to ascertain one or more trends in at least some of the plurality of different healthy building parameters. In some cases, this may include tracking the values of at least some of the plurality of different healthy building parameters over time in order to ascertain one or more trends in the airborne infection risk score.

The risk model ascertains an airborne infection risk score for at least part of the facility, as indicated at block 54*a*. The risk model may be used to ascertain one or more suggested changes to a current operation of the BMS system in order to reduce the airborne infection risk score, as indicated at block 54*b*. In some cases, one or more of the suggested changes to the current operation of the BMS system may be ascertained using machine learning. In some cases, the illustrative method 50 includes providing one or more operational commands to the BMS system in order to implement one or more of the suggested changes to the current operation of the BMS system, as indicated at block 56.

In particular cases, the BMS system includes a Heating, Ventilating and Air Conditioning (HVAC) system, and one of the suggested changes to the current operation of the BMS system may include one or more of changing a temperature in the facility using the HVAC system, changing a humidity level in the facility using the HVAC system, and changing a fresh air ventilation rate in the facility using the HVAC system. In some cases, an estimated expense to implement and/or operate in accordance with each of the suggested changes may be calculated and displayed, along with an expected improvement to the airborne infection risk score.

Figure 4:
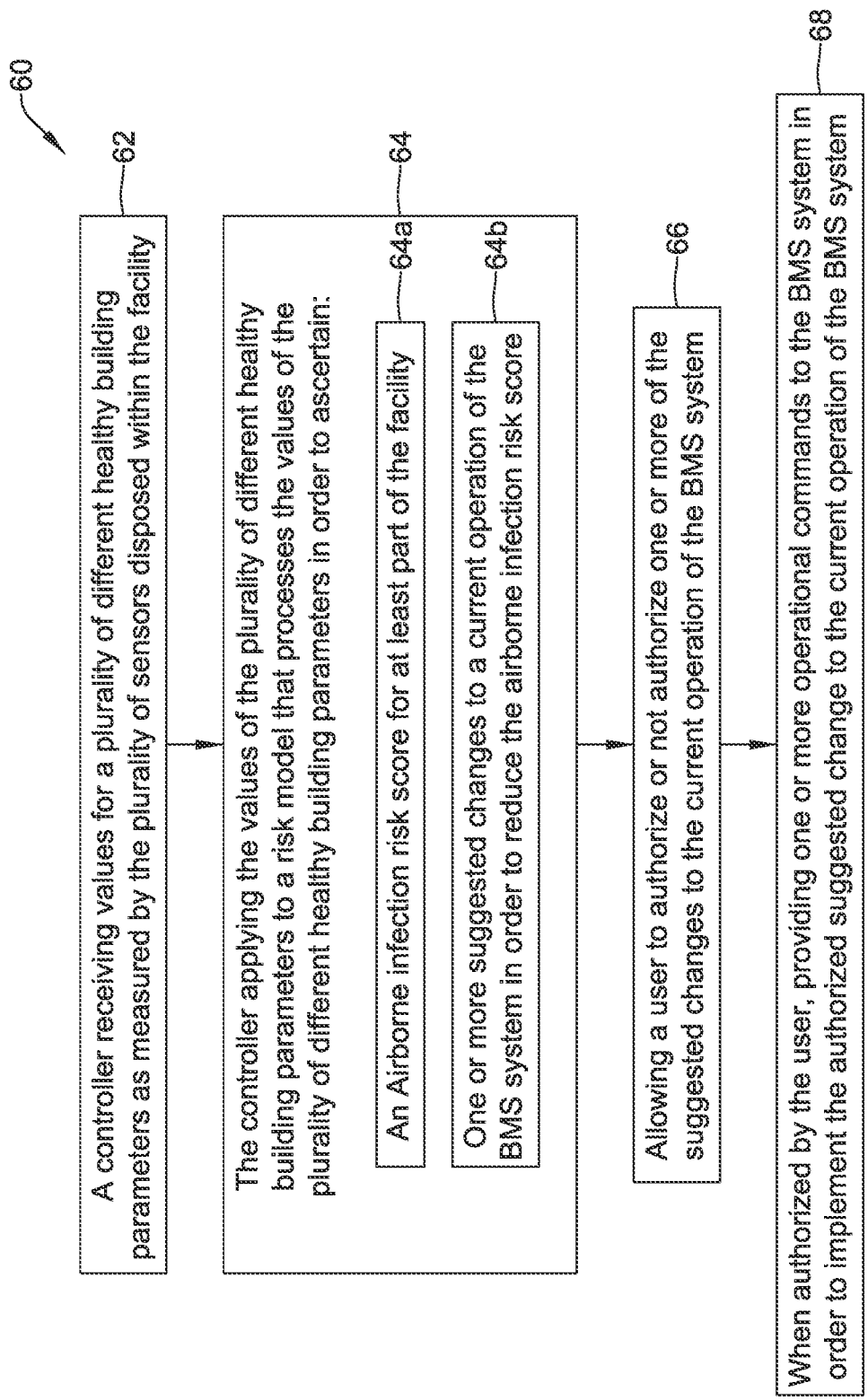
FIG. 4 is a flow diagram showing an illustrative method.

FIG. 4 is a flow diagram showing an illustrative method 60 for reducing risks of airborne infection within a facility having a Building Management System (BMS) with a plurality of sensors disposed within the facility configured to measure a plurality of different healthy building parameters that impact risk of airborne infection. The plurality of sensors may include a temperature sensor and a humidity sensor. The plurality of sensors may further include a particulate matter sensor and/or a total volatile organic compounds sensor. The plurality of sensors may further include a CO sensor and/or an occupancy sensor. In some cases, the plurality of sensors may further include a video camera.

The illustrative method 60 includes a controller (such as the controller 24) receiving values for a plurality of different healthy building parameters as measured by the plurality of sensors disposed within the facility, as indicated at block 62. The controller applies the values of the plurality of different healthy building parameters to a risk model that processes the values of the plurality of different healthy building parameters, as indicated at block 64. In some cases, this may include tracking the values of at least some of the plurality of different healthy building parameters over time in order to ascertain one or more trends in at least some of the plurality of different healthy building parameters. In some cases, this may include tracking the values of at least some of the plurality of different healthy building parameters over time in order to ascertain one or more trends in the airborne infection risk score.

The risk model ascertains an airborne infection risk score for at least part of the facility, as indicated at block 64a. The risk model may be used to ascertains one or more suggested changes to a current operation of the BMS system in order to reduce the airborne infection risk score, as indicated at block 64b. In some cases, one or more of the suggested changes to the current operation of the BMS system may be ascertained using machine learning. In some cases, an estimated expense to implement and/or operate in accordance with each of the suggested changes may be calculated and displayed, along with an expected improvement to the airborne infection risk score.

The illustrative method 60 includes allowing a user to authorize or not authorize one or more of the suggested changes to the current operation of the BMS system, as indicated at block 66. When authorized by the user, one or more operational commands are provided to the BMS system in order to implement the authorized suggested change to the current operation of the BMS system, as indicated at block 68. In particular cases, the BMS system includes a Heating, Ventilating and Air Conditioning (HVAC) system, and one of the suggested changes to the current operation of the BMS system may include one or more of changing a temperature in the facility using the HVAC system, changing a humidity level in the facility using the HVAC system, and changing a fresh air ventilation rate in the facility using the HVAC system.

Figure 5:
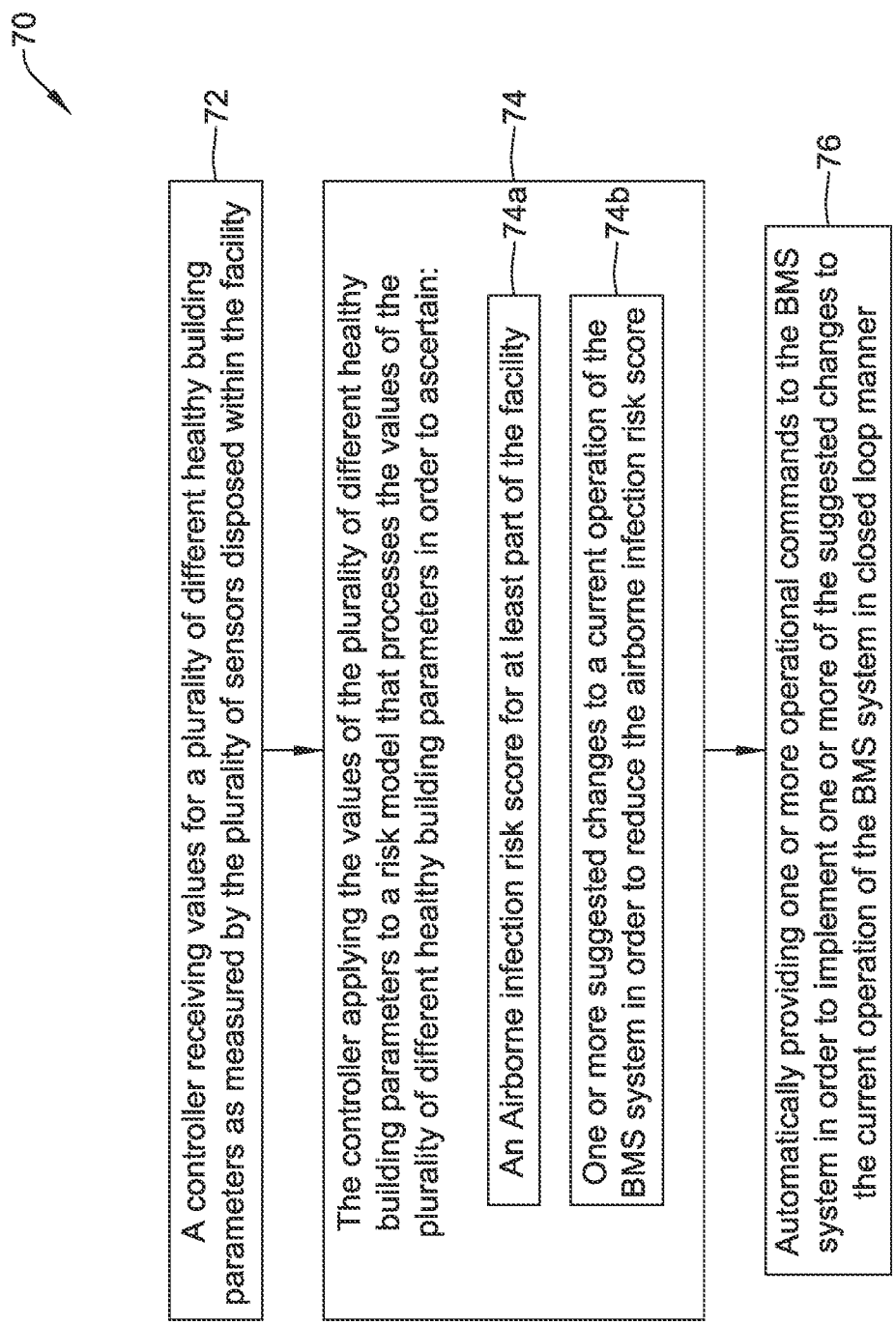
FIG. 5 is a flow diagram showing an illustrative method.

FIG. 5 is a flow diagram showing an illustrative method 70 for reducing risks of airborne infection within a facility having a Building Management System (BMS) with a plurality of sensors disposed within the facility configured to measure a plurality of different healthy building parameters that impact risk of airborne infection. The plurality of sensors may include a temperature sensor and a humidity sensor. The plurality of sensors may further include a particulate matter sensor and/or a total volatile organic compounds sensor. The plurality of sensors may further include a CO sensor and/or an occupancy sensor. In some cases, the plurality of sensors may further include a video camera.

The method 70 includes a controller (such as the controller 24) receiving values for a plurality of different healthy building parameters as measured by the plurality of sensors disposed within the facility, as indicated at block 72. The controller applies the values of the plurality of different healthy building parameters to a risk model that processes the values of the plurality of different healthy building parameters, as indicated at block 74. In some cases, this may include tracking the values of at least some of the plurality of different healthy building parameters over time in order to ascertain one or more trends in at least some of the plurality of different healthy building parameters. In some cases, this may include tracking the values of at least some of the plurality of different healthy building parameters over time in order to ascertain one or more trends in the airborne infection risk score.

The risk model ascertains an airborne infection risk score for at least part of the facility, as indicated at block 74a. The risk model may also be used to ascertains one or more suggested changes to a current operation of the BMS system in order to reduce the airborne infection risk score, as indicated at block 74b. The method 60 includes automatically providing one or more operational commands to the BMS system in order to implement one or more of the suggested changes to the current operation of the BMS system in a closed loop manner, as indicated at block 76. In some cases, one or more of the suggested changes to the current operation of the BMS system may be ascertained using machine learning. In particular cases, the BMS system includes a Heating, Ventilating and Air Conditioning (HVAC) system, and one of the suggested changes to the current operation of the BMS system may include one or more of changing a temperature in the facility using the HVAC system, changing a humidity level in the facility using the HVAC system, and changing a fresh air ventilation rate in the facility using the HVAC system.

Figure 6:
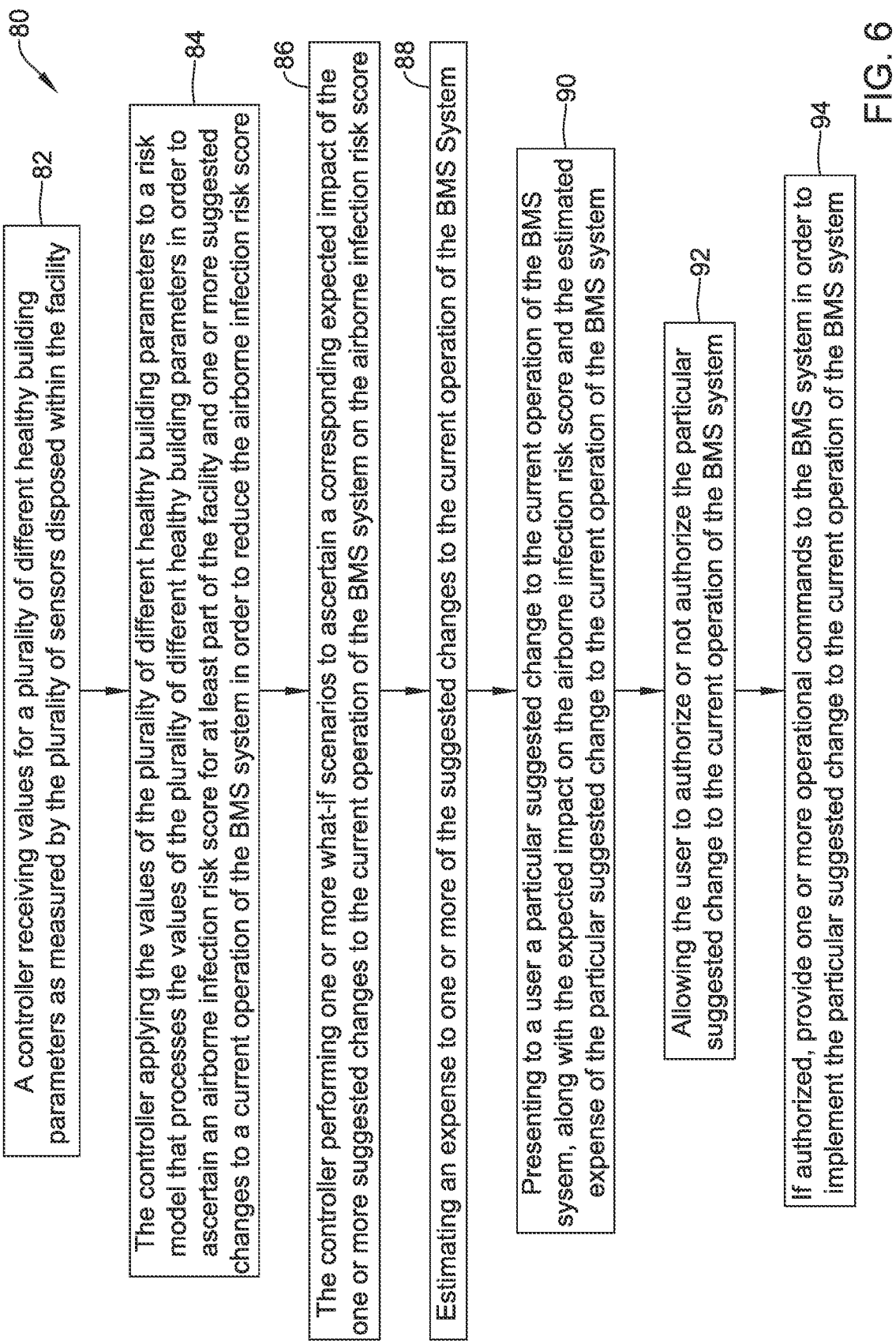
FIG. 6 is a flow diagram showing an illustrative method.

FIG. 6 is a flow diagram showing an illustrative method 80 for reducing risks of airborne infection within a facility having a Building Management System (BMS) with a plurality of sensors disposed within the facility configured to measure a plurality of different healthy building parameters that impact risk of airborne infection. The plurality of sensors may include a temperature sensor and a humidity sensor. The plurality of sensors may further include a particulate matter sensor and/or a total volatile organic compounds sensor. The plurality of sensors may further include a CO sensor and/or an occupancy sensor. In some cases, the plurality of sensors may further include a video camera.

The method 80 includes a controller (such as the controller 24) receiving values for a plurality of different healthy building parameters as measured by the plurality of sensors disposed within the facility, as indicated at block 82. The controller applies the values of the plurality of different healthy building parameters to a risk model that processes the values of the plurality of different healthy building parameters in order to ascertain an airborne infection risk score for at least part of the facility. The risk model may also be used to ascertain one or more suggested changes to a current operation of the BMS system in order to reduce the airborne infection risk score, as indicated at block 84. In some cases, one or more of the suggested changes to the current operation of the BMS system may be ascertained using machine learning. In particular cases, the BMS system includes a Heating, Ventilating and Air Conditioning (HVAC) system, and one of the suggested changes to the current operation of the BMS system may include one or more of changing a temperature in the facility using the HVAC system, changing a humidity level in the facility using the HVAC system, and changing a fresh air ventilation rate in the facility using the HVAC system.

The illustrative method 80 includes the controller performing one or more what-if scenarios to ascertain a corresponding expected impact of the one or more suggested changes to the current operation of the BMS system on the airborne infection risk score, as indicated at block 86. In some cases, and as indicated at block 88, the method 80 may include estimating an expense to one or more of the suggested changes to the current operation of the BMS system. The user may be presented with a particular suggested change to the current operation of the BMS system, along with the expected impact on the airborne infection risk score and the estimated expense of the particular suggested change to the current operation of the BMS system, as indicated at block 90. In some cases, and as indicated at block 92, the user may be allowed to authorize or not authorize the particular suggested change to the current operation of the BMS system. When authorized, one or more operational commands are provided to the BMS system in order to implement the particular suggested change to the current operation of the BMS system, as indicated at block 94.

In some cases, occupancy levels may be tracked over time in order to allow facility managers to provide improved building usage policies. This may be especially true during a pandemic, for example. Building usage policies may be revised in order to improve safety. By tracking occupancy levels over time, it may be possible to determine, for example, that reducing overall occupancy within a particular part of a building by a given percentage reduction may result in a corresponding reduction in the possible infection risk. Moreover, risk models may be used to trend infection risks that are based at least in part upon expected occupancy spikes, such as may occur during a townhall meeting or a large conference. This can also occur if a particular conference room is frequently booked and/or is even overpopulated. A facility manager can even simulate the infection risk, and the system can suggest a BMS strategy for the upcoming event, or even an UVC strategy.

FIG. 7 is a flow diagram showing an illustrative method 100 for reducing risks of airborne infection within a facility having a Building Management System (BMS) with a plurality of sensors disposed within the facility configured to measure a plurality of different healthy building parameters that impact risk of airborne infection. The plurality of sensors may include a temperature sensor and a humidity sensor. The method 100 includes a controller receiving values for a plurality of different healthy building parameters as measured by the plurality of sensors disposed within the facility, as indicated at block 102. The controller applies the values of the plurality of different healthy building parameters to a risk model that processes the values of the plurality of different healthy building parameters and ascertains an airborne infection risk score for at least part of the facility, as indicated at block 104. An alert is generated when the airborne infection risk score for at least part of the facility exceeds an infection risk score threshold, as indicated at block 106. In response, one or more pathogen tests are performed in the facility using one or more portable pathogen testing devices, as indicated at block 108. The one or more portable pathogen testing devices may include a Bio-disk and/or a cartridge-based portable pathogen testing device. Pathogen testing can be relatively expensive. Method 100 may be used to identify when conditions in the building are such that pathogen testing may be warranted. In some cases, the method 100 may also identify where in the building the pathogen testing should be performed.

FIG. 8 is a flow diagram showing an illustrative method 110 for reducing risks of airborne infection within a facility having a Building Management System (BMS) with a plurality of sensors disposed within the facility configured to measure a plurality of different healthy building parameters that impact risk of airborne infection. The plurality of sensors may include a temperature sensor and a humidity sensor. The method 110 includes a controller receiving values for a plurality of different healthy building parameters as measured by the plurality of sensors disposed within the facility, as indicated at block 112. The controller applies the values of the plurality of different healthy building parameters to a risk model that processes the values of the plurality of different healthy building parameters and ascertains an airborne infection risk score for at least two regions of the facility, as indicated at block 114. A respective alert is generated when the airborne infection risk score for each of the at least two regions of the facility exceeds a corresponding infection risk score threshold, as indicated at block 116. In response, one or more pathogen tests are performed in the corresponding region of the facility using one or more portable pathogen testing devices, as indicated at block 118. The one or more portable pathogen testing devices may include a Bio-disk and/or a cartridge-based portable pathogen testing device.

FIG. 9 is a flow diagram showing an illustrative method 120 for identifying risks of airborne infection within a facility having a Building Management System (BMS) with a plurality of sensors disposed within the facility configured to measure a plurality of different healthy building parameters that impact risk of airborne infection. The method 120 includes a controller receiving values for a plurality of different healthy building parameters as measured by the plurality of sensors disposed within the facility, as indicated at block 122. The control applies the values of the plurality of different healthy building parameters to a risk model that processes the values of the plurality of different healthy building parameters and ascertains an airborne infection risk score for each of at least two regions of the facility and also ascertains an overall airborne infection risk score for the facility, wherein the overall airborne infection risk score for the facility is dependent on the airborne infection risk scores for each of the at least two regions of the facility, as indicated at block 124. The overall airborne infection risk score for the facility is displayed on a dashboard, as indicated at block 126.

From the dashboard, an input is accepted from a user, wherein responsive to receiving the input from the user, displaying the airborne infection risk score for one or more of the at least two regions of the facility, as indicated at block 128. In some cases, the input from the user may be a request to drill down to a selected one of the at least two regions of the facility, and responsive to receiving the input from the user, the airborne infection risk score for the selected one of the at least two regions of the facility is displayed. In some cases, the overall airborne infection risk score for the facility is an aggregation of the airborne infection risk scores for each of the at least two regions of the facility.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method for reducing risks of airborne infection within a facility having a Building Management System (BMS) with a plurality of sensors disposed within each of two or more regions of the facility, the BMS configured to measure a plurality of different healthy building parameters that impact risk of airborne infection in each of the two or more regions of the facility, the method comprising:
   a controller receiving values for a plurality of different healthy building parameters for each of the two or more regions of the facility as measured by the plurality of sensors disposed within each of the two or more regions of the facility;
   the controller applying the values of the plurality of different healthy building parameters to a risk model that processes the values of the plurality of different healthy building parameters in order to ascertain:
      an airborne infection risk score for each of the two or more regions of the facility;
      an overall airborne infection risk score for the facility, wherein the overall airborne infection risk score for the facility is dependent on the airborne infection risk scores for each of the at least two regions of the facility;
      a respective alert for each of the two or more regions of the facility when the corresponding airborne infection risk score exceeds a corresponding infection risk score threshold;
   the controller displaying the overall airborne infection risk score for the facility on a dashboard;
   from the dashboard, the controller accepting an input from a user to drill down to a selected one of the at least two regions of the facility, wherein responsive to receiving the input from the user, displaying the airborne infection risk score for at least the selected one of the at least two regions of the facility; and
   responsive to a respective alert, the controller displaying the respective alert on the dashboard.

2. The method of claim 1, wherein the risk model processing the values of the plurality of different healthy building parameters comprises tracking the values of at least some of the plurality of different healthy building parameters over time in order to ascertain one or more trends in at least some of the plurality of different healthy building parameters.

3. The method of claim 2, wherein the risk model processing the values of the plurality of different healthy building parameters comprises tracking the values of at least some of the plurality of different healthy building parameters over time in order to ascertain one or more trends in the airborne infection risk score.

4. The method of claim 1, wherein the risk model processes the values of the plurality of different healthy building parameters in order to ascertain one or more suggested changes to a current operation of the BMS system in order to reduce the airborne infection risk score, and wherein the controller using the risk model to perform one or more what-if scenarios to ascertain a corresponding expected impact of the one or more suggested changes to the current operation of the BMS system on the airborne infection risk score.

5. The method of claim 4, wherein the controller further comprising estimating an expense to one or more of the suggested changes to the current operation of the BMS system, and presenting to a user a particular suggested change to the current operation of the BMS system on the dashboard, along with the expected impact on the airborne infection risk score and the estimated expense of the particular suggested change to the current operation of the BMS system.

6. The method of claim 5, wherein the controller further comprising allowing the user to authorize or not authorize the particular suggested change to the current operation of the BMS system, and if authorized, provide one or more operational commands to the BMS system in order to implement the particular suggested change to the current operation of the BMS system.

7. The method of claim 1, wherein the plurality of sensors comprise a temperature sensor and a humidity sensor.

8. The method of claim 7, wherein the plurality of sensors further comprise a particulate matter sensor, a total volatile organic compounds sensor, a CO sensor and/or an occupancy sensor.

9. The method of claim 1, wherein responsive to a respective alert, performing one or more pathogen tests on the environment in the corresponding region of the facility using one or more portable pathogen testing devices to confirm that the corresponding region has an elevated risk of airborne infection.

10. The method of claim 7, wherein the plurality of sensors further comprise a video camera.

11. The method of claim 1, wherein the risk model processes the values of the plurality of different healthy building parameters in order to ascertain one or more suggested changes to a current operation of the BMS system in order to reduce the airborne infection risk score, and wherein the controller allowing a user to authorize or not authorize one or more of the suggested changes to the current operation of the BMS system, and if authorized by the user, providing one or more operational commands to the BMS system in order to implement the authorized suggested change to the current operation of the BMS system.

12. The method of claim 1, wherein the risk model processes the values of the plurality of different healthy building parameters in order to ascertain one or more suggested changes to a current operation of the BMS system in order to reduce the airborne infection risk score, and wherein responsive to ascertaining the one or more suggested changes to the current operation of the BMS system in order to reduce the airborne infection risk score, automatically providing one or more operational commands to the BMS system in order to implement one or more of the suggested changes to the current operation of the BMS system in a closed loop manner.

13. The method of claim 1, wherein the risk model processes the values of the plurality of different healthy building parameters in order to ascertain one or more suggested changes to a current operation of the BMS system in order to reduce the airborne infection risk score, and wherein one or more of the suggested changes to the current operation of the BMS system is ascertained using machine learning.

14. The method of claim 1, wherein the risk model processes the values of the plurality of different healthy building parameters in order to ascertain one or more suggested changes to a current operation of the BMS system in order to reduce the airborne infection risk score, and wherein the BMS system includes a Heating, Ventilating and Air Conditioning (HVAC) system, and one of the suggested changes to the current operation of the BMS system comprises one or more of changing a temperature in the facility using the HVAC system, changing a humidity level in the facility using the HVAC system, and changing a fresh air ventilation rate in the facility using the HVAC system.

15. A method for reducing risks of airborne infection within a facility having a Building Management System (BMS) with a plurality of sensors disposed within each of two or more regions of the facility, the BMS configured to measure a plurality of different healthy building parameters that impact risk of airborne infection in each of the two or more regions of the facility, the method comprising:
   a controller receiving values for a plurality of different healthy building parameters for each of the two or more regions of the facility as measured by the plurality of sensors disposed within each of the two or more regions of the facility;
   the controller applying the values of the plurality of different healthy building parameters to a risk model that processes the values of the plurality of different healthy building parameters and ascertains an airborne infection risk score for each of the two or more regions of the facility;
   generating a respective alert for each of the two or more regions of the facility when the corresponding airborne infection risk score exceeds a corresponding infection risk score threshold; and
   responsive to a respective alert, performing one or more pathogen tests on the environment in the corresponding region of the facility using one or more portable pathogen testing devices to confirm that the corresponding region has an elevated risk of airborne infection.

16. The method of claim 15, wherein the plurality of sensors comprise a temperature sensor and a humidity sensor, and the one or more portable pathogen testing devices comprises a Bio-disk and/or cartridge based portable pathogen testing device.

17. A method for identifying risks of airborne infection within a facility having a Building Management System (BMS) with a plurality of sensors disposed within the facility configured to measure a plurality of different healthy building parameters that impact risk of airborne infection, the method comprising:
   a controller receiving values for a plurality of different healthy building parameters as measured by the plurality of sensors disposed within the facility;
   the controller applying the values of the plurality of different healthy building parameters to a risk model that processes the values of the plurality of different healthy building parameters and ascertains an airborne infection risk score for each of at least two regions of the facility and also ascertains an overall airborne infection risk score for the facility, wherein the overall airborne infection risk score for the facility is dependent on the airborne infection risk scores for each of the at least two regions of the facility;
   displaying the overall airborne infection risk score for the facility on a dashboard; and
   from the dashboard, accepting an input from a user to drill down to a selected one of the at least two regions of the facility, wherein responsive to receiving the input from the user, displaying the airborne infection risk score for at least the selected one of the at least two regions of the facility.

18. The method of claim 17, wherein the overall airborne infection risk score for the facility is an aggregation of the airborne infection risk scores for each of the at least two regions of the facility.

* * * * *